(12) United States Patent
Nakafuji et al.

(10) Patent No.: US 12,265,333 B2
(45) Date of Patent: Apr. 1, 2025

(54) COMPOSITION, RESIST UNDERLAYER FILM, METHOD OF FORMING RESIST UNDERLAYER FILM, METHOD OF PRODUCING PATTERNED SUBSTRATE, AND COMPOUND

(71) Applicant: JSR CORPORATION, Tokyo (JP)

(72) Inventors: Shin-ya Nakafuji, Tokyo (JP); Tomoaki Taniguchi, Tokyo (JP); Kazunori Takanashi, Tokyo (JP)

(73) Assignee: JSR CORPORATION, Tokyo (JP)

( * ) Notice: Subject to any disclaimer, the term of this patent is extended or adjusted under 35 U.S.C. 154(b) by 504 days.

(21) Appl. No.: 17/482,557

(22) Filed: Sep. 23, 2021

(65) Prior Publication Data

US 2022/0011672 A1 Jan. 13, 2022

Related U.S. Application Data

(63) Continuation of application No. PCT/JP2020/014140, filed on Mar. 27, 2020.

(30) Foreign Application Priority Data

Mar. 28, 2019 (JP) ................. 2019-063609

(51) Int. Cl.
*G03F 7/11* (2006.01)
*C07C 39/21* (2006.01)
(Continued)

(52) U.S. Cl.
CPC ............... *G03F 7/11* (2013.01); *C07C 39/21* (2013.01); *C07C 39/225* (2013.01);
(Continued)

(58) Field of Classification Search
None
See application file for complete search history.

(56) References Cited

U.S. PATENT DOCUMENTS

2016/0085152 A1\* 3/2016 Nakafuji ................. C07C 33/28
430/323
2018/0348633 A1\* 12/2018 Wakamatsu ............. G03F 7/30
2018/0356731 A1\* 12/2018 Tagawa ................ G03F 7/0392

FOREIGN PATENT DOCUMENTS

| JP | 2004177668 A | 6/2004 |
| KR | 20160023696 A | 3/2016 |
| WO | WO-2018019436 A1 | 2/2018 |

OTHER PUBLICATIONS

Beillard, A., Métro, T.-X., Bantreil, X., Martinez, J. and Lamaty, F. (2017), A3-Coupling Reaction and [Ag(IPr)2]PF6: A Successful Couple. Eur. J. Org. Chem., 2017: 4642-4647. (Year: 2017).\*

(Continued)

*Primary Examiner* — Sean M DeGuire
*Assistant Examiner* — Andrew Preston Traywick
(74) *Attorney, Agent, or Firm* — Element IP, PLC

(57) ABSTRACT

The composition contains: a compound which has a group represented by formula (1); and a solvent. In the formula (1), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; and \* denotes a bonding site to a part other than the group represented by the following formula (1) in the compound.

16 Claims, 1 Drawing Sheet

(51) Int. Cl.
  C07C 39/225    (2006.01)
  C07C 211/54    (2006.01)
  C07D 207/323   (2006.01)
  C07D 307/36    (2006.01)
  C08G 8/10      (2006.01)
  C09D 161/06    (2006.01)

(52) U.S. Cl.
  CPC ........ *C07C 211/54* (2013.01); *C07D 207/323* (2013.01); *C07D 307/36* (2013.01); *C08G 8/10* (2013.01); *C09D 161/06* (2013.01); *C07C 2603/18* (2017.05); *C07C 2603/26* (2017.05); *C07C 2603/50* (2017.05)

(56) References Cited

OTHER PUBLICATIONS

Correia, C. and Li, C.-J. (2010), Copper-Catalyzed Cross-Dehydrogenative Coupling (CDC) of Alkynes and Benzylic C—H Bonds. Adv. Synth. Catal., 352: 1446-1450. (Year: 2010).*

Supporting Information Document for Correia et al (Year: 2010).*

Gopiraman et al (Mayakrishnan Gopiraman, Dian Deng, Sundaram Ganesh Babu, Takuya Hayashi, Ramasamy Karvembu, and Ick Soo Kim, ACS Sustainable Chemistry & Engineering 2015 3 (10), 2478-2488 (Year: 2015).*

Rubial et al (Rubial, B., Ballesteros, A. and González, J.M. (2013), Gold(I)-Catalyzed Bis-Alkynylation Reaction of Aromatic Aldehydes with Alkynylsilanes. Adv. Synth. Catal., 355: 3337-3343) (Year: 2013).*

And Dutta et al (Ranjan Dutta, Srinivas Samala, Hongil Jo, Kang Min Ok, and Chang-Hee Lee, The Journal of Organic Chemistry 2019 84 (11), 6851-6857 (Year: 2019).*

International Search Report issued Jun. 9, 2020 in PCT/IP2020/014140 (with English translation), 7 pages.

Written Opinion of the International Searching Authority issued Jun. 9, 2020 in PCT/JP2020/014140 (with English translation), 10 pages.

Office Action issued Mar. 30, 2023 in Japanese Patent Application No. 2021-509650 (with English translation), 8 pages.

Office Action issued Aug. 29, 2023 in Japanese Patent Application No. 2021-509650 (with English translation), 4 pages.

Office Action issued May 22, 2024 in corresponding Korean Patent Application No. 10-2021-7030418 (with machine English translation), 22 pages.

* cited by examiner

COMPOSITION, RESIST UNDERLAYER FILM, METHOD OF FORMING RESIST UNDERLAYER FILM, METHOD OF PRODUCING PATTERNED SUBSTRATE, AND COMPOUND

CROSS-REFERENCE TO RELATED APPLICATIONS

The present application is a continuation application of International Application No. PCT/JP2020/014140, filed Mar. 27, 2020, which claims priority to Japanese Patent Application No. 2019-063609, filed Mar. 28, 2019. The contents of these applications are incorporated herein by reference in their entirety.

BACKGROUND OF THE INVENTION

Field of the Invention

The present invention relates to a composition, a resist underlayer film, a method of forming a resist underlayer film, a method of producing a patterned substrate, and a compound.

Description of the Related Art

In manufacturing semiconductor devices, for example, a multilayer resist process has been employed in which a resist film laminated on a substrate via a resist underlayer film, e.g., an organic underlayer film or a silicon-containing film, is exposed and developed to form a resist pattern. In this process, the resist underlayer film is etched by using the resist pattern as a mask and etching is further carried out using the resultant resist underlayer film pattern as a mask, whereby a desired pattern can be formed on the substrate, thereby enabling obtaining a patterned substrate (see Japanese Unexamined Patent Application, Publication No. 2004-177668).

SUMMARY OF THE INVENTION

According to an aspect of the present invention, a composition includes: a compound which includes a group represented by formula (1); and a solvent.

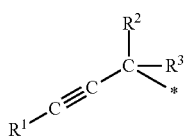

(1)

In the formula (1), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; and * denotes a binding site to a part other than the group represented by the formula (1) in the compound.

According to another aspect of the present invention, a method of forming a resist underlayer film includes applying the above-mentioned composition directly or indirectly on a substrate.

According to a further aspect of the present invention, a method of producing a patterned substrate includes: forming a resist underlayer film directly or indirectly on a substrate by applying the above-mentioned composition; forming a resist pattern directly or indirectly on the resist underlayer film; and carrying out etching using the resist pattern as a mask.

According to a further aspect of the present invention, a compound is represented by formula (2).

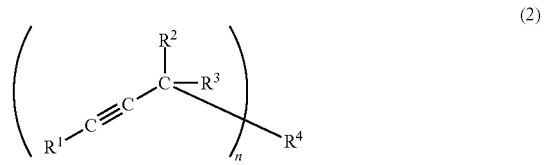

(2)

In the formula (2), $R^1$ and $R^2$ each independently represent a substituted or unsubstituted aryl group having 6 to 30 ring atoms or a substituted or unsubstituted heteroaryl group having 5 to ring atoms; $R^3$ represents a hydrogen atom or a substituted or unsubstituted monovalent aliphatic hydrocarbon group having 1 to 10 carbon atoms; n is an integer of 1 to 10, wherein in a case in which n is no less than 2, a plurality of $R^1$s are identical or different from each other, a plurality of $R^2$s are identical or different from each other, and a plurality of $R^3$s are identical or different from each other; and in a case in which n is 1, $R^4$ represents a hydrogen atom or a monovalent organic group having 1 to 40 carbon atoms, and in a case in which n is no less than 2, $R^4$ represents an organic group having a valency of n and having 1 to 40 carbon atoms.

DESCRIPTION OF EMBODIMENTS

Figure 1:
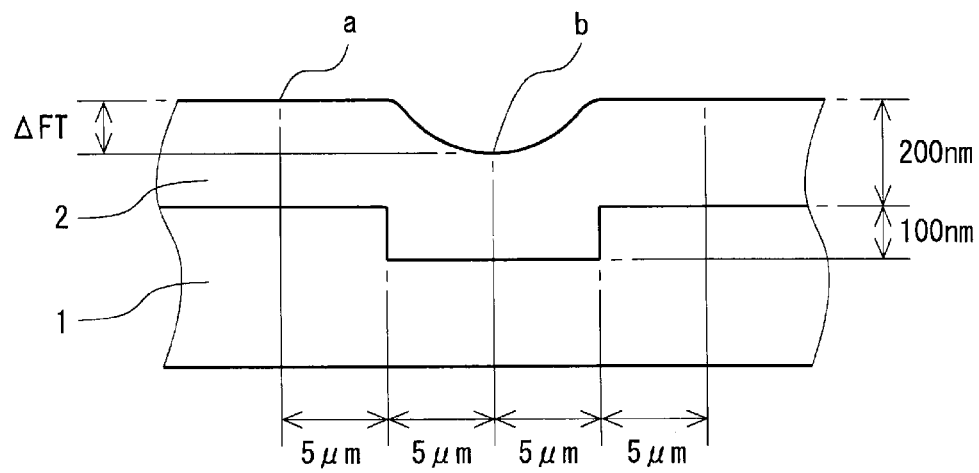
FIG. 1 is a schematic cross-sectional view for illustrating a flatness evaluation method.

In a multilayer resist process, etching resistance and heat resistance are required for the organic underlayer film. Furthermore, the organic underlayer film is required to have superior flatness.

Furthermore, in etching a substrate using the organic underlayer film pattern formed as a mask, the organic underlayer film is required to be less likely to bend, i.e., to be superior in flexural resistance. It is to be noted that each of the etching resistance, heat resistance, flatness, and flexural resistance is explained along with evaluation standards in Examples, described later.

One embodiment of the invention is a composition for forming a resist underlayer film, the composition containing: a compound (hereinafter, may be also referred to as "(A) compound" or "compound (A)") which has a group represented by the following formula (1); and a solvent (hereinafter, may be also referred to as "(B) solvent" or "solvent (B)").

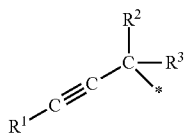
(1)

In the formula (1), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; and * denotes a binding site to a part other than the group represented by the formula (1) in the compound.

Another embodiment of the invention is a resist underlayer film formed from the composition for forming a resist underlayer film of the embodiment of the present invention.

Still another embodiment of the invention is a method of forming a resist underlayer film including a step of applying the composition for forming a resist underlayer film of the embodiment of the present invention directly or indirectly on a substrate.

Yet another embodiment of the invention is a method of producing a patterned substrate, the method including steps of: forming a resist underlayer film directly or indirectly on a substrate by applying the composition for forming a resist underlayer film of the embodiment of the present invention; forming a resist pattern directly or indirectly on the resist underlayer film; and carrying out etching using the resist pattern as a mask.

A further embodiment of the invention is a compound represented by the following formula (2).

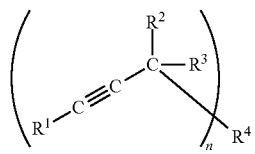
(2)

In the formula (2), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; n is an integer of 1 to 10, wherein in a case in which n is no less than 2, a plurality of $R^1$s are identical or different from each other, a plurality of $R^2$s are identical or different from each other, and a plurality of $R^3$s are identical or different from each other; and in a case in which n is 1, $R^4$ represents a hydrogen atom or a monovalent organic group having 1 to 40 carbon atoms, and in a case in which n is no less than 2, $R^4$ represents an organic group having a valency of n and having 1 to 40 carbon atoms.

The composition for forming a resist underlayer film of the embodiment of the present invention enables forming a resist underlayer film being superior in etching resistance, heat resistance, flatness, and flexural resistance. The resist underlayer film of the embodiment of the present invention is superior in etching resistance, heat resistance, flatness, and flexural resistance. The method of forming a resist underlayer film of the embodiment of the invention enables forming a resist underlayer film being superior in etching resistance, heat resistance, flatness, and flexural resistance. The method of forming a patterned substrate of the embodiment of the present invention enables obtaining a favorable patterned substrate. The compound of the embodiment of the present invention can be favorably used as a component of the composition for forming a resist underlayer film of the embodiment of the present invention. Therefore, these can be suitably used in the manufacture of semiconductor devices and the like, in which further progress of miniaturization is expected in the future. Hereinafter, the embodiments of the present invention will be explained in detail.

Composition for Forming Resist Underlayer Film

A composition for forming a resist underlayer film of the embodiment of the present invention (hereinafter, may be also referred to simply as the "composition") contains the compound (A) and the solvent (B). In addition to the compound (A) and the solvent (B), the composition may contain, within a range not leading to impairment of the effects of the present invention, other optional component(s).

Due to containing the compound (A), the composition enables forming a resist underlayer film being superior in etching resistance, heat resistance, flatness, and flexural resistance. Thus, the composition can be suitably used in a multilayer resist process.

Each component contained in the composition will be described below.

(A) Compound

The compound (A) has a group (hereinafter, may be also referred to as "group (I)") represented by the following formula (1). The composition may contain one, or two or more types of the compound (A).

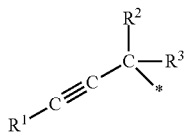
(1)

In the above formula (1), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; and * denotes a binding site to a part other than the group represented by the formula (1) in the compound.

Due to containing the compound (A), the composition enables forming a resist underlayer film being superior in etching resistance, heat resistance, flatness, and flexural resistance. Although not necessarily clarified and without wishing to be bound by any theory, the reason for achieving the effects described above due to the composition having the constitution described above may be supposed as in the following, for example. It is considered that due to the group (I) in the compound (A) having a carbon-carbon triple bond, the resist underlayer film formed by the composition is superior in etching resistance, heat resistance, and flexural resistance, and further, the group (I) in the compound (A) has a carbon atom having an $SP^3$ hybrid orbital (a carbon atom to which $R^1$—C≡C—, $R^2$, and $R^3$ bond in the above formula (1)), whereby rigidity of the compound (A)

becomes comparatively low, which is considered to lead to the resist underlayer film formed from the composition being superior in flatness.

The number of "ring atoms" as referred to herein means the number of atoms constituting a ring structure, and in the case of a polycyclic ring structure, the number of "ring atoms" means the number of atoms constituting the polycyclic ring. The "aliphatic hydrocarbon group" as referred to herein may be exemplified by a chain hydrocarbon group and an alicyclic hydrocarbon group. The "chain hydrocarbon group" as referred to herein means an aliphatic hydrocarbon group not including a cyclic structure but being constituted with only a chain structure, and examples thereof include a linear hydrocarbon group and a branched hydrocarbon group. The "alicyclic hydrocarbon group" as referred to herein means a hydrocarbon group that includes, as a ring structure, not an aromatic ring structure but an alicyclic structure alone, and examples thereof include both a monocyclic alicyclic hydrocarbon group and a polycyclic alicyclic hydrocarbon group (wherein these groups are not necessarily constituted by an alicyclic structure alone, and may include a chain structure in a part thereof).

The unsubstituted aryl group having 6 to 30 ring atoms which may be represented by $R^1$ or $R^2$ is exemplified by a phenyl group, a naphthyl group, an anthryl group, a fluorenyl group, a phenanthryl group, a phenalenyl group, a pyrenyl group, a chrysenyl group, a triphenylenyl group, a tetracenyl group, a perylenyl group, a picenyl group, a pentacenyl group, a hexacenyl group, a coronenyl group, a trinaphthylenyl group, a heptacenyl group, and the like.

The unsubstituted heteroaryl group having 5 to 30 ring atoms which may be represented by $R^1$ or $R^2$ may be exemplified by a pyrrolyl group, a pyridyl group, a furyl group, a thiophenyl group, and the like.

The unsubstituted monovalent aliphatic hydrocarbon group having 1 to 10 carbon atoms which may be represented by $R^3$ is exemplified by a monovalent chain hydrocarbon group having 1 to 10 carbon atoms, a monovalent alicyclic hydrocarbon group having 3 to 10 carbon atoms, and the like.

Examples of the monovalent chain hydrocarbon group having 1 to 10 carbon atoms include groups obtained from: alkanes such as methane, ethane, propane, and butane; alkenes such as ethene, propene, and butene; alkynes such as ethyne, propyne and butyne; and the like by removing one hydrogen atom included therein, and the like.

Examples of the monovalent alicyclic hydrocarbon group having 3 to 10 carbon atoms include groups obtained from: alicyclic saturated hydrocarbons, e.g., cycloalkanes such as cyclopentane and cyclohexane, and bridged cyclic saturated hydrocarbons such as norbornane and adamantane; cycloalkenes such as cyclopentene and cyclohexene; bridged cyclic unsaturated hydrocarbons such as norbornene; and the like by removing one hydrogen atom included therein, and the like.

Examples of a substituent in $R^1$ to $R^3$ include: halogen atoms such as a fluorine atom, a chlorine atom, a bromine atom, and an iodine atom; alkoxy groups such as a methoxy group, an ethoxy group, and a propoxy group; alkoxycarbonyl groups such as a methoxycarbonyl group and an ethoxycarbonyl group; alkoxycarbonyloxy groups such as a methoxycarbonyloxy group and an ethoxycarbonyloxy group; acyl groups such as a formyl group, an acetyl group, a propionyl group, and a butyryl group; a cyano group; a nitro group; a monovalent chain hydrocarbon group having 1 to 10 carbon atoms; and the like.

$R^1$ and $R^2$ each represent preferably the substituted or unsubstituted aryl group having 6 to 30 ring atoms, more preferably at least one of $R^1$ and $R^2$ represents the substituted aryl group having 6 to 30 ring atoms, and still more preferably at least one of $R^1$ and $R^2$ represents a group represented by the following formula (3).

In the above formula (3), $R^5$ represents a hydrogen atom or a monovalent aliphatic hydrocarbon group having 1 to 10 carbon atoms; Ar represents a group obtained by removing (m+1) hydrogen atoms from an aromatic ring having 6 to 30 ring atoms; m is an integer of 1 to 3; ** denotes a binding site to a carbon atom to which $R^1$ or $R^2$ bonds in the above formula (1); and in a case in which m is no less than 2, a plurality of $R^5$s are identical or different from each other.

Examples of the monovalent aliphatic hydrocarbon group having 1 to 10 carbon atoms which may be represented by $R^5$ include groups similar to those exemplified as the unsubstituted monovalent aliphatic hydrocarbon group having 1 to 10 carbon atoms which may be represented by $R^3$ in the above formula (1).

Examples of the aromatic ring having 6 to 30 ring atoms in Ar include: aromatic hydrocarbon rings such as a benzene ring, a naphthalene ring, an anthracene ring, an indene ring, a pyrene ring, a fluorenylidenebiphenyl ring, and a fluorenylidenebinaphthalene ring; aromatic heterorings such as a furan ring, a pyrrole ring, a thiophene ring, a phosphole ring, a pyrazole ring, an oxazole ring, an isoxazole ring, a thiazole ring, a pyridine ring, a pyrazine ring, a pyrimidine ring, a pyridazine ring, and a triazine ring; and the like.

$R^5$ represents preferably a hydrogen atom.

Ar represents preferably a group obtained by removing (m+1) hydrogen atoms from an aromatic hydrocarbon ring, and more preferably a group obtained by removing (m+1) hydrogen atoms from benzene.

m is preferably 1 or 2.

$R^3$ represents preferably a hydrogen atom or a substituted or unsubstituted monovalent chain hydrocarbon group having 1 to 10 carbon atoms, more preferably a hydrogen atom or an unsubstituted monovalent chain hydrocarbon group having 1 to 10 carbon atoms, and still more preferably a hydrogen atom.

The group (I) is preferably, for example, a group (may be also referred to as group (I-1) to (I-8)) represented by the following formulae (I-1) to (I-8).

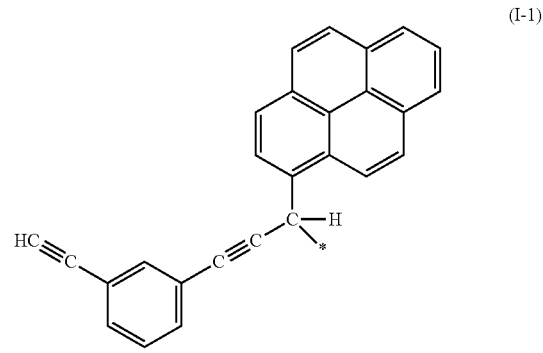

(I-2)

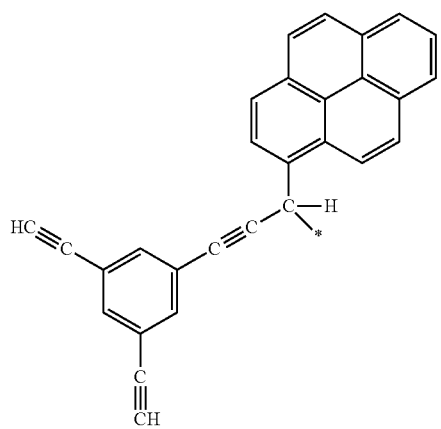

(I-3)

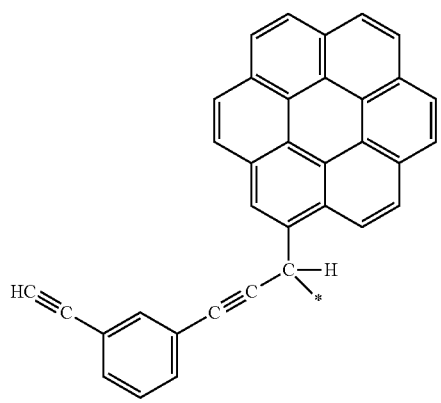

(I-4)

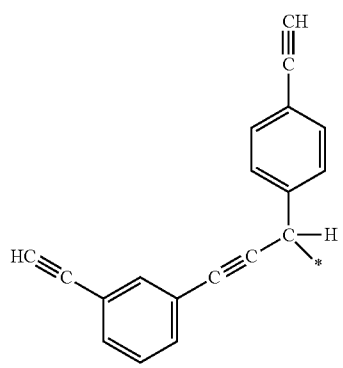

(I-5)

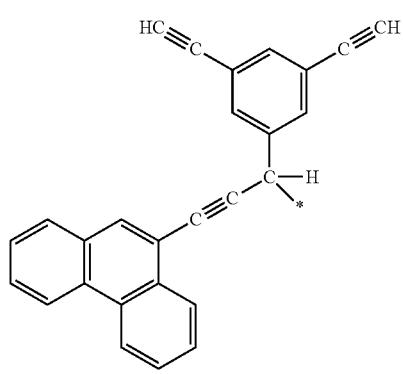

(I-6)

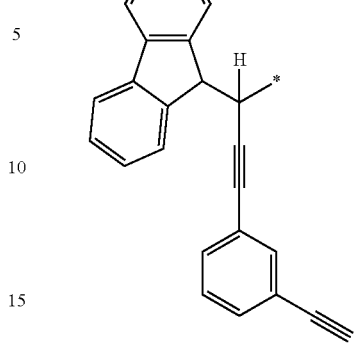

(I-7)

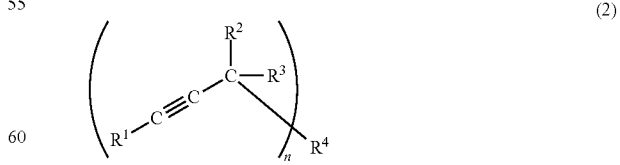

(I-8)

In the above formulae (I-1) to (I-8), * denotes a binding site to a part other than the groups represented by the above formulae (I-1) to (I-8) in the compound.

The compound (A) is preferably a compound represented by the following formula (2).

$$\left( R^1-C\equiv C-\underset{R^4}{\overset{R^2}{\underset{|}{C}}}-R^3 \right)_n$$

(2)

In the above formula (2), $R^1$ and $R^2$ each independently represent a substituted or unsubstituted aryl group having 6 to 30 ring atoms or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; n is an integer of 1 to 10, wherein in a case in which n is no less than 2, a plurality of $R^1$s are identical or different from each other, a plurality of $R^2$s are identical or different from each other, and a plurality of $R^3$s are identical or different from each other; and in a case in which n is 1, $R^4$ represents a hydrogen atom or a monovalent organic group having 1 to 40 carbon atoms, and in a case in which n is no less than 2, $R^4$ represents an organic group having a valency of n and having 1 to 40 carbon atoms.

$R^1$ to $R^3$ in the above formula (2) are defined similarly to $R^1$ to $R^3$ in the above formula (1).

The "organic group" as referred to herein means a group that includes at least one carbon atom. The organic group having a valency of n and having 1 to 40 carbon atoms which may be represented by $R^4$ is exemplified by: a hydrocarbon group having a valency of n and having 1 to 40 carbon atoms; a group having a divalent hetero atom-containing group between two adjacent carbon atoms of the hydrocarbon group having a valency of n and having 1 to 40 carbon atoms; a group obtained by substituting with a monovalent substituent having a hetero atom, a part or all of hydrogen atoms included in the hydrocarbon group having a valency of n and having 1 to 40 carbon atoms or the divalent hetero atom-containing group; and the like.

Examples of the divalent hetero atom-containing group include —CO—, —CS—, —NH—, —O—, —S—, a combination thereof, and the like.

Examples of the monovalent substituent having a hetero atom include a hydroxy group, a sulfanyl group, a cyano group, a nitro group, a halogen atom, and the like.

n is preferably no less than 2, more preferably 2 to 4, and still more preferably 2 or 3.

$R^4$ represents preferably the organic group having a valency of n and having 1 to 40 carbon atoms, more preferably an organic group having a valency of n and including an aromatic ring having 5 to 40 ring atoms, and still more preferably a group (may be also referred to as groups (II-1) to (II-5)) represented by the following formulae (II-1) to (II-5).

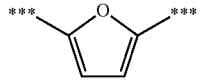
(II-1)

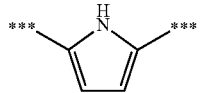
(II-2)

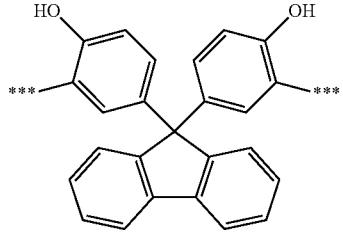
(II-3)

(II-4)

(II-5)

In the above formulae (II-1) to (II-5), *** denotes a binding site to a carbon atom to which $R^4$ in the above formula (2) bonds.

Examples of the compound (A) include compounds (hereinafter, may be also referred to as "compounds (A-1) to (A-8)") represented by the following formulae (A-1) to (A-8), and the like.

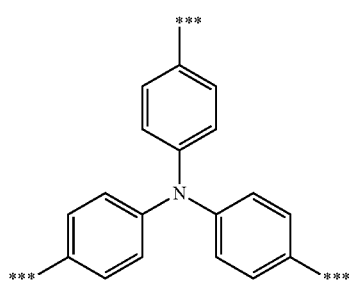
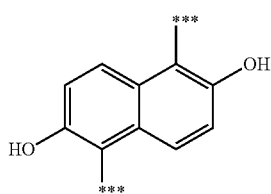
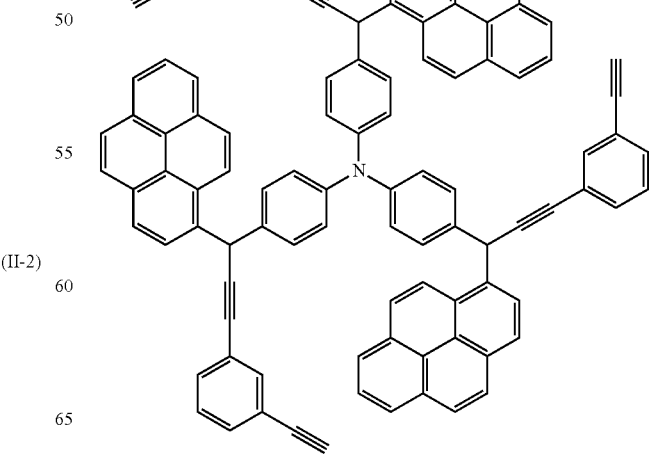
(A-1)

(A-2)
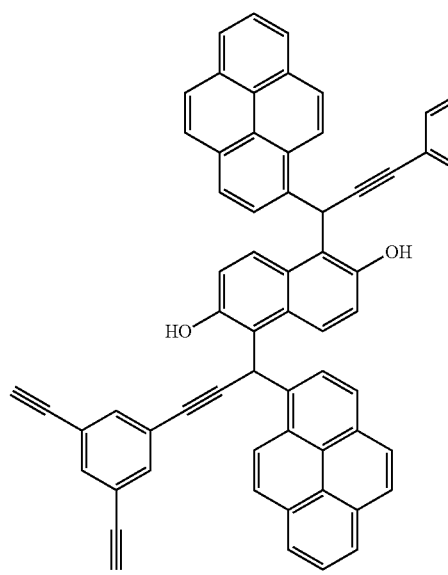
(A-3)
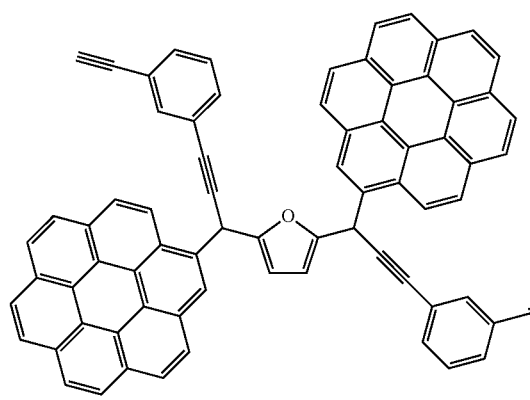
(A-4)
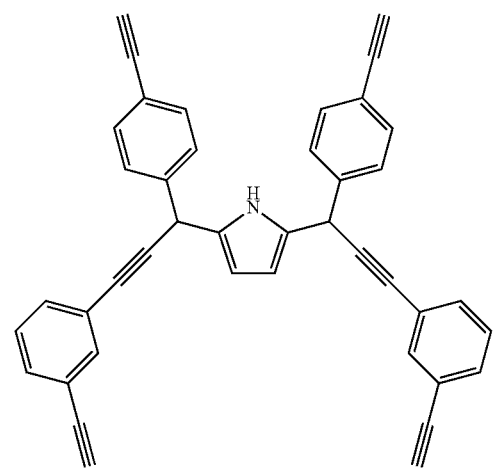
(A-5)
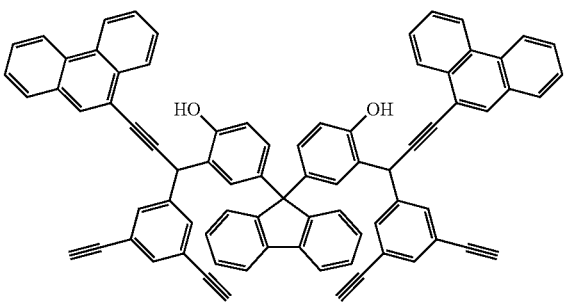
(A-6)
(A-7)
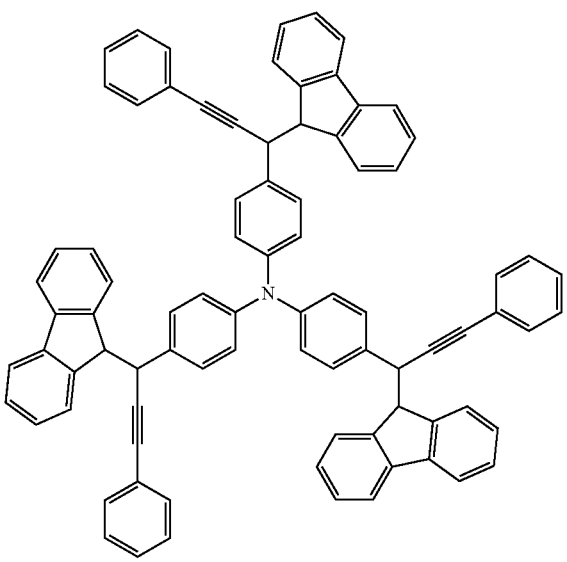

-continued

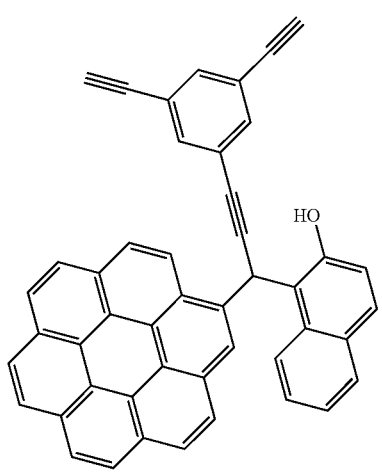

(A-8)

The upper limit of a proportion of hydrogen atoms with respect to total atoms constituting the compound (A) is preferably 7% by mass, more preferably 6% by mass, and still more preferably 5% by mass. The lower limit of the proportion is, for example, 0.1% by mass. When the proportion of hydrogen atoms with respect to total atoms constituting the compound (A) falls within the above range, the flexural resistance of the resist underlayer film formed from the composition can be further improved. It is to be noted that the proportion of hydrogen atoms with respect to total atoms constituting the compound (A) is a value calculated from a molecular formula of the compound (A).

The lower limit of a molecular weight of the compound (A) is preferably 300, more preferably 400, and still more preferably 500. The upper limit of the molecular weight is preferably 3,000, more preferably 2,500, and still more preferably 2,000. When the molecular weight of the compound (A) falls within the above range, the flatness of the resist underlayer film formed from the composition can be further improved.

The lower limit of a proportion of the compound (A) with respect to total components other than the solvent (B) in the composition is preferably 50% by mass, more preferably 60% by mass, and still more preferably 70% by mass.

Synthesis Procedure of Compound (A)

The compound (A) can be synthesized by, for example, a procedure of reacting a compound having a carbon-carbon triple bond such as m-diethynylbenzene, 1,3,5-triethylbenzene, or 9-ethynylphenanthrene with an aldehyde compound such as 1-formylpyrene, 1-coronenecarbaldehyde, p-trimethylsilylethynylbenzaldehyde, or 3,5-bis(trimethylsilylethynyl)benzaldehyde to synthesize an intermediate compound that gives the group (I), and reacting the thus obtained intermediate compound with a compound that gives $R^4$ in the above formula (2) such as triphenylamine, 2,6-dihydroxynaphthalene, furan, pyrrole, or 9,9-bis(4-hydroxyphenyl)fluorine.

(B) Solvent

The solvent (B) is not particularly limited as long as it is capable of dissolving or dispersing the compound (A) and the optional component(s), which is/are contained as needed.

The solvent (B) is exemplified by an ester solvent, an alcohol solvent, a ketone solvent, an ether solvent, a nitrogen-containing solvent, and the like. The solvent (B) may be used either alone of one type, or in a combination of two or more types thereof.

Examples of the ester solvent include: carbonate solvents such as diethyl carbonate; mono ester acetate solvents such as methyl acetate and ethyl acetate; lactone solvents such as γ-butyrolactone; polyhydric alcohol partial ether carboxylate solvents such as diethylene glycol monomethyl ether acetate and propylene glycol monomethyl ether acetate; ester lactate solvents such as methyl lactate and ethyl lactate; and the like.

Examples of the alcohol solvent include: monohydric alcohol solvents such as methanol, ethanol, and n-propanol; polyhydric alcohol solvents such as ethylene glycol and 1,2-propylene glycol; and the like.

Examples of the ketone solvent include: chain ketone solvents such as methyl ethyl ketone and methyl isobutyl ketone; cyclic ketone solvents such as cyclohexanone; and the like.

Examples of the ether solvent include: polyhydric alcohol ether solvents, e.g., chain ether solvents such as n-butyl ether, and cyclic ether solvents such as tetrahydrofuran; polyhydric alcohol partial ether solvents such as diethylene glycol monomethyl ether; and the like.

Examples of the nitrogen-containing solvent include: chain nitrogen-containing solvents such as N,N-dimethylacetamide; cyclic nitrogen-containing solvents such as N-methylpyrrolidone; and the like.

The solvent (B) is preferably the ester solvent or the ketone solvent, more preferably the polyhydric alcohol partial ether carboxylate solvent or the cyclic ketone solvent, and still more preferably propylene glycol monomethyl ether acetate or cyclohexanone.

The lower limit of a proportion of the solvent (B) in the composition is preferably 50% by mass, more preferably 60% by mass, and still more preferably 70% by mass. The upper limit of the proportion is preferably 99.9% by mass, more preferably 99% by mass, and still more preferably 95% by mass.

Optional Component(s)

The composition may contain, as optional component(s), an acid generating agent (hereinafter, may be also referred to as "(C) acid generating agent" or "acid generating agent (C)"), a crosslinking agent (hereinafter, may be also referred to as "(D) crosslinking agent" or "crosslinking agent (D)"), a surfactant, and the like. These optional component(s) may be used either alone of one type, or in a combination of two or more types thereof.

(C) Acid Generating Agent

The acid generating agent (C) is a component which generates an acid by an action of a radioactive ray or heat. When the composition contains the acid generating agent (C), a crosslinking reaction of the compound (A) and the like is promoted by the acid generated, whereby an increase in the hardness of the resist underlayer film formed by the composition is enabled. The acid generating agent (C) may be used either alone of one type, or in a combination of two or more types thereof.

The acid generating agent (C) is exemplified by an onium salt compound, an N-sulfonyloxyimide compound, and the like.

Examples of the onium salt compound include a sulfonium salt, a tetrahydrothiophenium salt, an iodonium salt, an ammonium salt, and the like.

Examples of the sulfonium salt include triphenylsulfonium trifluoromethanesulfonate, triphenylsulfonium nonafluoro-n-butanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium 2-bicyclo[2.2.1]hept-2-yl-1,1,2,2-tetrafluoroethanesulfonate, and the like.

Examples of the iodonium salt include diphenyliodonium trifluoromethanesulfonate, diphenyliodonium nonafluoro-n-butanesulfonate, bis(4-t-butylphenyl)iodonium nonafluoro-n-butanesulfonate, bis(4-t-butylphenyl)iodonium 2-bicyclo[2.2.1]hept-2-yl-1,1,2,2-tetrafluoroethanesulfonate, and the like.

Examples of the ammonium salt include triethylammonium trifluoromethanesulfonate, triethylammonium nonafluoro-n-butanesulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

The acid generating agent (C) is preferably the onium salt compound, more preferably the iodonium salt, and still more preferably bis(4-t-butylphenyl)iodonium nonafluoro-n-butanesulfonate.

In the case in which the composition contains the acid generating agent (C), the lower limit of a content of the acid generating agent (C) with respect to 100 parts by mass of the compound (A) is preferably 0.1 parts by mass, more preferably 0.5 parts by mass, and still more preferably 1 part by mass. The upper limit of the content is preferably 30 parts by mass, more preferably 20 parts by mass, and still more preferably 10 parts by mass. When the content of the acid generating agent (C) falls within the above range, an increase in the hardness of the resist underlayer film formed by the composition is enabled.

(D) Crosslinking Agent

The crosslinking agent (D) forms crosslinking bonds between molecules of the compound (A) contained in the composition, or forms crosslinked structures by its own molecules, through an action of heat and/or an acid. When the composition contains the crosslinking agent (D), an increase in the hardness of the resist underlayer film formed is enabled. The crosslinking agent (D) may be used either alone of one type, or in a combination of two or more types thereof.

The crosslinking agent is exemplified by polyfunctional (meth)acrylate compounds, epoxy compounds, hydroxymethyl group-substituted phenol compounds, alkoxyalkyl group-containing phenol compounds, compounds having an alkoxyalkylated amino group, compounds (hereinafter, may be also referred to as "compounds (D1) to (D5)") represented by the following formulae (D1) to (D5), and the like.

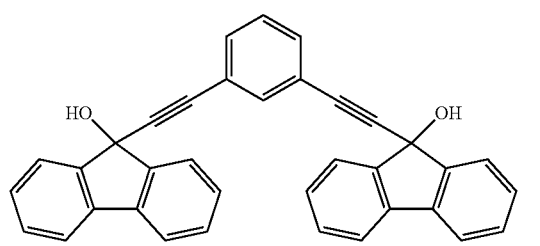
(D1)

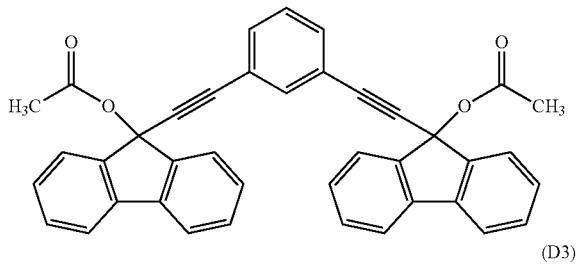
(D2)

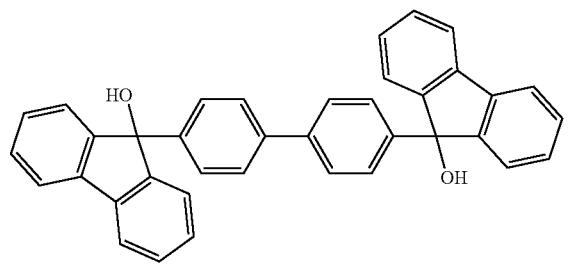
(D3)

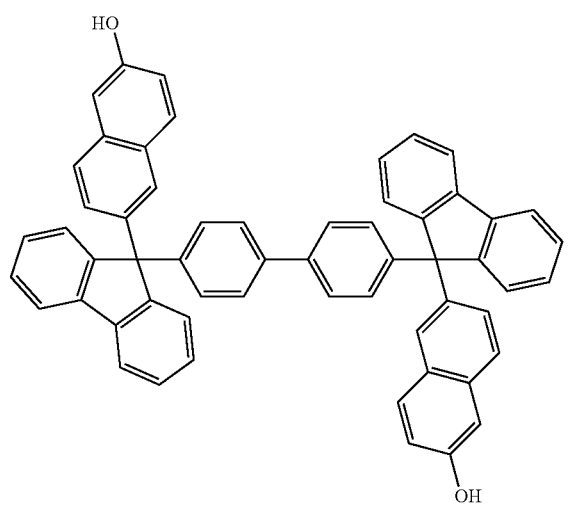
(D4)

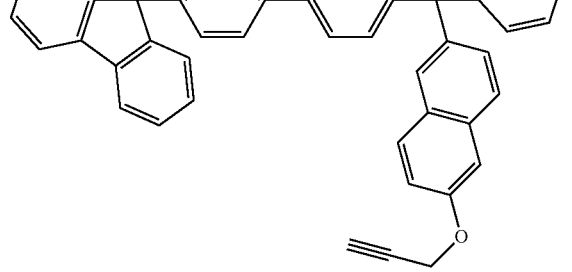
(D5)

Examples of the polyfunctional (meth)acrylate compound include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, bis(2-hydroxyethyl)isocyanurate di(meth)acrylate, and the like.

Examples of the epoxy compound include novolac epoxy resins, bisphenol epoxy resins, alicyclic epoxy resins, aliphatic epoxy resins, and the like.

Examples of the hydroxymethyl group-substituted phenol compound include 2-hydroxymethyl-4,6-dimethylphenol, 1,3,5-trihydroxymethylbenzene, 3,5-dihydroxymethyl-4-methoxytoluene [2,6-bis(hydroxymethyl)-p-cresol], and the like.

Examples of the alkoxyalkyl group-containing phenol compounds include methoxymethyl group-containing phenol compounds, ethoxymethyl group-containing phenol compounds, and the like.

The compound having an alkoxyalkylated amino group is exemplified by nitrogen-containing compounds having a plurality of active methylol groups in a molecule thereof wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas, and the like. It is to be noted that a mixture in which a plurality of substituted compounds have been mixed may be used as the compound having an alkoxyalkylated amino group, and the compound having an alkoxyalkylated amino group may contain an oligomer component formed through partial self-condensation thereof.

The crosslinking agent (D) is preferably the compound having an alkoxyalkylated amino group, and more preferably 1,3,4,6-tetrakis(methoxymethyl)glycoluril.

In the case in which the composition contains the crosslinking agent (D), the lower limit of a content of the crosslinking agent (D) with respect to 100 parts by mass of the compound (A) is preferably 1 part by mass, more preferably 5 parts by mass, and still more preferably 10 parts by mass. The upper limit of the content is preferably 100 parts by mass, more preferably 50 parts by mass, and still more preferably 40 parts by mass. When the content of the crosslinking agent (D) falls within the above range, an increase in the hardness of the resist underlayer film formed by the composition for forming a resist underlayer film is enabled.

Preparation Procedure of Composition for Forming Resist Underlayer Film

The composition may be prepared by mixing the compound (A) and the solvent (B), as well as the optional component(s) as needed, in a certain ratio, and preferably filtering a thus resulting mixture through a membrane filter having a pore size of no greater than 0.1 m.

Resist Underlayer Film

The resist underlayer film of the embodiment of the present invention is formed from the composition of the embodiment of the present invention. The resist underlayer film is superior in etching resistance, heat resistance, flatness, and flexural resistance.

Method of Forming Resist Underlayer Film

The method of forming a resist underlayer film of the embodiment of the present invention includes a step (hereinafter, may be also referred to as "applying step") of applying the composition of the embodiment of the present invention directly or indirectly on a substrate. The case of applying the composition indirectly on the substrate may be exemplified by a case of applying the composition on a silicon-containing film, described later, which has been formed on the substrate.

Due to using the composition in the applying step, the method of forming a resist underlayer film enables forming a resist underlayer film being superior in etching resistance, heat resistance, flatness, and flexural resistance.

It is preferred that the method of forming a resist underlayer film further includes a step (hereinafter, may be also referred to as "heating step") of heating a coating film formed by the applying step.

Hereinafter, each step will be described.

Applying Step

In this step, the composition is applied directly or indirectly on the substrate. An applying procedure is not particularly limited, and for example, an appropriate procedure such as spin coating, cast coating, or roll coating may be employed. By this step, a coating film is formed, and by occurrence of, e.g., a crosslinking reaction of the compound (A) and volatilization of the solvent (B) contained in the coating film, the resist underlayer film is formed.

Examples of the substrate include metal and metalloid substrates such as a silicon substrate, an aluminum substrate, a nickel substrate, a chrome substrate, a molybdenum substrate, a tungsten substrate, a copper substrate, a tantalum substrate, and a titanium substrate, and of these, the silicon substrate is preferred. The substrate may also be provided with a silicon nitride film, an alumina film, a silicon dioxide film, a tantalum nitride film, a titanium nitride film, or the like formed thereon.

Heating Step

In this step, the coating film formed in the applying step is heated. By this step, formation of the resist underlayer film is promoted.

The heating of the coating film is typically carried out in an ambient air, but may be carried out in a nitrogen atmosphere. The lower limit of a temperature in the heating is preferably 150° C., and more preferably 200° C. The upper limit of the temperature is preferably 600° C., and more preferably 400° C. The lower limit of a time period of the heating is preferably 15 sec, and more preferably 30 sec. The upper limit of the time period is preferably 1,200 sec, and more preferably 600 sec.

It is to be noted that in this step, the resist underlayer film is formed through the heating of the coating film; however, in a case in which the composition contains the acid generating agent (C) and the acid generating agent (C) is a radiation-sensitive acid generating agent, formation of the resist underlayer film may be further promoted through a combination of an exposure and heating. The radioactive ray which can be used for the exposure may be appropriately selected in accordance with a type of the acid generating agent, and examples thereof include: electromagnetic waves such as a visible light ray, an ultraviolet ray, a far ultraviolet ray, an X-ray, and a γ-ray; particle rays such as an electron beam, a molecular beam, and an ion beam; and the like.

The lower limit of an average thickness of the resist underlayer film to be formed is preferably 30 nm, more preferably 50 nm, and still more preferably 100 nm. The upper limit of the average thickness is preferably 3,000 nm, more preferably 2,000 nm, and still more preferably 500 nm. It is to be noted that the average thickness of the resist underlayer film is a value obtained by: using a spectroscopic ellipsometer ("M2000D," available from J. A. Woollam) to measure film thicknesses at nine locations of the resist underlayer film, and calculating an average value of these film thicknesses.

Method of Producing Patterned Substrate

The method of producing a patterned substrate of the embodiment of the present invention includes: a step (hereinafter, may be also referred to as "applying step") of forming a resist underlayer film directly or indirectly on a substrate by applying the composition of the embodiment of the present invention; a step (hereinafter, may be also referred to as "resist pattern-forming step") of forming a resist pattern directly or indirectly on the resist underlayer film; and a step (hereinafter, may be also referred to as "etching step") of carrying out etching using the resist pattern as a mask.

According to the method of producing a patterned substrate, a resist underlayer film being superior in etching resistance, heat resistance, flatness, and flexural resistance is formed in the applying step; thus, the method of producing a patterned substrate enables producing a patterned substrate having a favorable pattern configuration.

The method of forming a patterned substrate may further include, as needed, a step (hereinafter, may be also referred to as "heating step") of heating a coating film formed by the applying step.

The method of forming a patterned substrate may further include, as needed, a step (hereinafter, may be also referred to as "silicon-containing film-forming step") of forming a silicon-containing film directly or indirectly on the resist underlayer film provided after the applying step or the heating step.

Hereinafter, each step will be described.

Applying Step

In this step, the composition of the embodiment of the invention is applied directly or indirectly on the substrate. This step is similar to the applying step in the method of producing a resist underlayer film of the embodiment of the present invention described above.

Heating Step

In this step, the coating film formed in the applying step is heated. This step is similar to the heating step in the method of producing a resist underlayer film described above.

Silicon-Containing Film-Forming Step

In this step, a silicon-containing film is formed directly or indirectly on the resist underlayer film provided after the applying step or the heating step. The case of forming the silicon-containing film indirectly on the resist underlayer film may be exemplified by a case in which a resist-underlayer-film-surface modification film has been formed on the resist underlayer film. The resist-underlayer-film-surface modification film is a film having, for example, an angle of contact with water being different from that of the resist underlayer film.

The silicon-containing film may be formed by applying a composition for forming a silicon-containing film, a chemical vapor deposition (CVD) procedure, atomic layer deposition (ALD), or the like. A procedure of forming the silicon-coating film by applying the composition for silicon-containing film formation is exemplified by: applying the composition for silicon-containing film formation directly or indirectly on the resist underlayer film to form a coating film; and hardening the coating film by subjecting the coating film to an exposure and/or heating. As a commercially available product of the composition for silicon-containing film formation, for example, "NFC SOG01," "NFC SOG04," or "NFC SOG080" (all available from JSR Corporation), or the like may be used. A silicon oxide film, a silicon nitride film, a silicon oxynitride film, or an amorphous silicon film can be formed by the chemical vapor deposition (CVD) procedure or the atom layer deposition (ALD).

Examples of the radioactive ray which may be used for the exposure include: electromagnetic waves such as a visible light ray, an ultraviolet ray, a far ultraviolet ray, an X-ray, and a $\gamma$-ray; particle rays such as an electron beam, a molecular beam, and an ion beam; and the like.

The lower limit of a temperature when subjecting the coating film to heating is preferably 90° C., more preferably 150° C., and still more preferably 200° C. The upper limit of the temperature is preferably 550° C., more preferably 450° C., and still more preferably 300° C. The lower limit of an average thickness of the silicon-containing film to be formed is preferably 1 nm, more preferably 10 nm, and still more preferably 20 nm. The upper limit of the average thickness is preferably 20,000 nm, more preferably 1,000 nm, and still more preferably 100 nm. It is to be noted that similar to the average thickness of the resist underlayer film, the average thickness of the silicon-containing film is measured using the spectroscopic ellipsometer.

Resist Pattern-Forming Step

In this step, the resist pattern is formed directly or indirectly on the resist underlayer film. In carrying out this step, for example, a resist composition may be used, a nanoimprinting procedure may be adopted, or a directed self-assembling composition may be used. The case of forming the resist pattern indirectly on the resist underlayer film may be exemplified by a case in which the resist pattern is formed on the silicon-containing film in the case in which the method of producing the patterned substrate includes the silicon-containing film-forming step, and the like.

With regard to using the resist composition, specifically, the resist film is formed by: applying the resist composition such that a resultant resist film has a predetermined thickness and thereafter subjecting the resist composition to prebaking to evaporate the solvent in the coating film.

Examples of the resist composition include a chemically amplified positive or negative resist composition that contains a radiation-sensitive acid generating agent; a positive resist composition that contains an alkali-soluble resin and a quinone diazide-based photosensitizing agent; a negative resist that contains an alkali-soluble resin and a crosslinking agent; and the like.

The lower limit of a proportion of total components other than the solvent in the resist composition is preferably 0.3% by mass, and more preferably 1% by mass. The upper limit of the proportion is preferably 50% by mass, and more preferably 30% by mass. Moreover, the resist composition is generally used for forming a resist film, for example, after being filtered through a filter with a pore size of no greater than 0.2 m. It is to be noted that a commercially available resist composition may be used as is in this step.

A procedure for applying the resist composition may be exemplified by, e.g., spin coating and the like. A temperature and time period of prebaking may be appropriately adjusted in accordance with the type of the resist composition employed and the like. The lower limit of the temperature is preferably 30° C., and more preferably 50° C. The upper limit of the temperature is preferably 200° C., and more preferably 150° C. The lower limit of the time period is preferably 10 sec, and more preferably 30 sec. The upper limit of the time period is preferably 600 sec, and more preferably 300 sec.

Next, the resist film formed is exposed by selective irradiation with a radioactive ray. The radioactive ray used in the exposure may be appropriately selected in accordance with the type of the radiation-sensitive acid generating agent used in the resist composition, and examples of the radioactive ray include: electromagnetic waves such as visible rays, ultraviolet rays, far ultraviolet rays, X-rays, and γ radiations; and particle rays such as electron beams, molecular beams, and ion beams. Among these, far ultraviolet rays are preferred, a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm), or an extreme ultraviolet ray (wavelength: 13.5 nm, etc.; hereinafter, may be also referred to as "EUV") is more preferred, and a KrF excimer laser beam, an ArF excimer laser beam, or EUV is still more preferred.

Post-baking may be carried out after the exposure for the purpose of improving a resolution, a pattern profile, developability, and the like. A temperature of the post-baking may be appropriately adjusted in accordance with the type of the resist composition employed and the like; however, the lower limit of the temperature is preferably 50° C., and more preferably 70° C. The upper limit of the temperature is preferably 200° C., and more preferably 150° C. The lower limit of a time period of the post-baking is preferably 10 sec, and more preferably 30 sec. The upper limit of the time period is preferably 600 sec, and more preferably 300 sec.

Next, the resist film exposed is developed with a developer solution to form a resist pattern. The development may be carried out by either development with an alkali, or development with an organic solvent. In the case of the development with an alkali, examples of the developer solution include a basic aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene, or the like. To the basic aqueous solution, a water-soluble organic solvent, for example, alcohols such as methanol and ethanol, a surfactant, etc., may be added, each in an appropriate amount. Alternatively, in the case of the development with an organic solvent, examples of the developer solution include various organic solvents exemplified as the solvent (B) of the composition described above, and the like.

A predetermined resist pattern is formed by the development with the developer solution, followed by washing and drying.

Etching Step

In this step, etching is carried out with the resist pattern as a mask. The etching may be conducted once or multiple times. In other words, the etching may be conducted sequentially with patterns obtained by the etching as masks, and in light of obtaining a pattern having a more favorable shape, the etching is preferably conducted multiple times. In the case in which the etching is conducted multiple times, the silicon-containing film, the resist underlayer film, and the substrate are subjected to the etching sequentially in this order. An etching procedure may be exemplified by dry etching, wet etching, and the like. Of these, in light of making the shape of the substrate pattern more favorable, the dry etching is preferred. In the dry etching, for example, gas plasma such as oxygen plasma, or the like may be used. By the etching, the patterned substrate having a predetermined pattern can be obtained.

The dry etching may be conducted by using, for example, a well-known dry etching apparatus. An etching gas to be used for the dry etching may be appropriately selected depending on the mask pattern, element composition of the film to be etched, and the like. Examples of the etching gas include: fluorine-based gases such as $CHF_3$, $CF_4$, $C_2F_6$, $C_3F_8$, and $SF_6$; chlorine-based gases such as $Cl_2$ and $BCl_3$; oxygen-based gases such as $O_2$, $O_3$, and $H_2O$; reductive gases such as $H_2$, $NH_3$, CO, $CO_2$, $CH_4$, $C_2H_2$, $C_2H_4$, $C_2H_6$, $C_3H_4$, $C_3H_6$, $C_3H_8$, HF, HI, HBr, HCl, NO, $NH_3$, and $BCl_3$; inert gases such as He, $N_2$, and Ar; and the like. These gases may be used as a mixture. In the case of etching the substrate using the resist underlayer film pattern as a mask, the fluorine-based gas is typically used.

Compound

The compound of the embodiment of the present invention is represented by the above formula (2). The compound can be suitably used as a component of the composition of the embodiment of the present invention. The compound has been described as the aforementioned compound (A).

EXAMPLES

Hereinafter, the present invention is explained in further detail by way of Examples, but the present invention is not in any way limited to these Examples. Measuring methods for various types of physical properties are shown below.

Weight Average Molecular Weight (Mw)

The Mw of a polymer (a-1) was measured by gel permeation chromatography (detector: differential refractometer) using GPC columns available from Tosoh Corporation ("G2000 HXL"×2 and "G3000 HXL"×1) under an analytical condition involving a flow rate of 1.0 mL/min, an elution solvent of tetrahydrofuran, and a column temperature of 40° C., with mono-dispersed polystyrene as a standard.

Average Thickness of Resist Underlayer Film

The average thickness of the resist underlayer film was measured using a spectroscopic ellipsometer ("M2000D," available from J. A. Woollam). The average thickness of the resist underlayer film is a value obtained by: using the spectroscopic ellipsometer ("M2000D," available from J. A. Woollam) to measure film thicknesses of nine locations of the resist underlayer film, and calculating an average value of these film thicknesses.

Synthesis of Compound (A)

Compounds (hereinafter, may be also referred to as "compounds (A-1) to (A-7)") represented by the following formulae (A-1) to (A-7), a polymer (hereinafter, may be also referred to as "polymer (a-1)") represented by the following formula (a-1), and compounds (hereinafter, may be also referred to as "compounds (a-2) and (a-3)") represented by the following formulae (a-2) and (a-3) were each synthesized in accordance with the procedures indicated below.

(A-1)
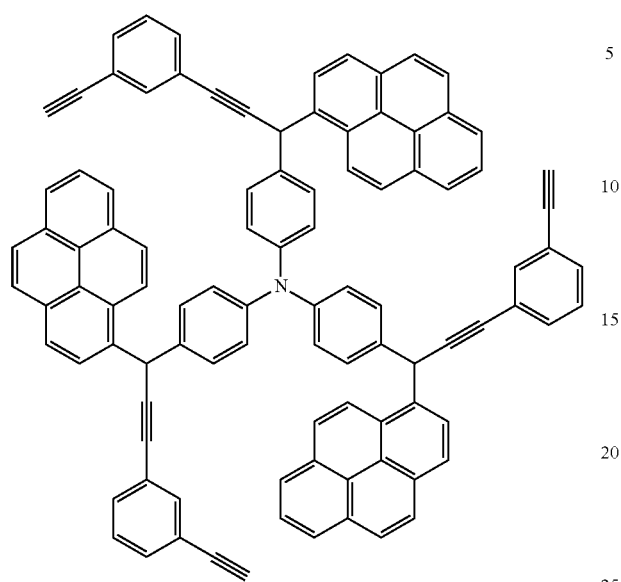
(A-4)
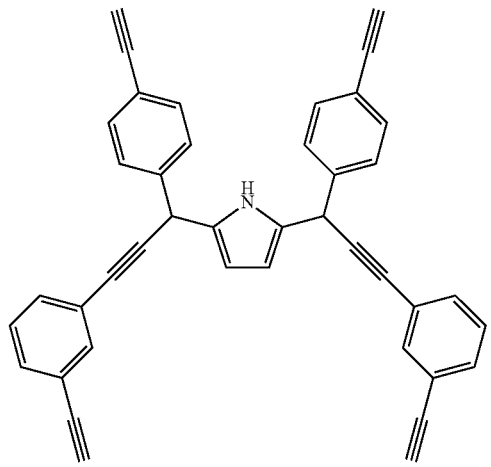
(A-2)
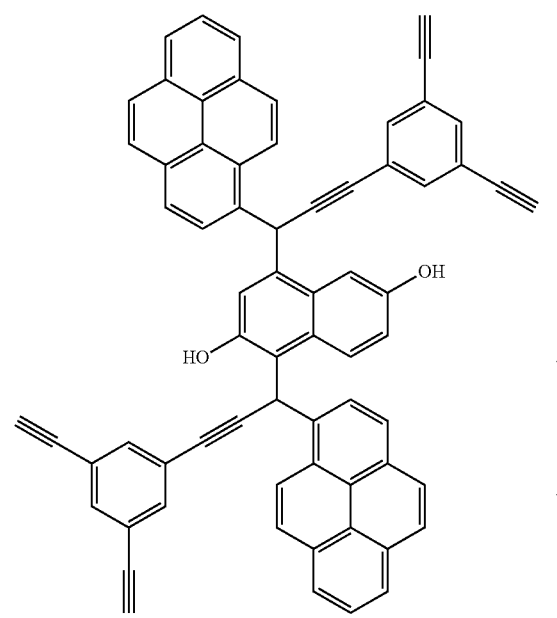
(A-5)
(A-3)
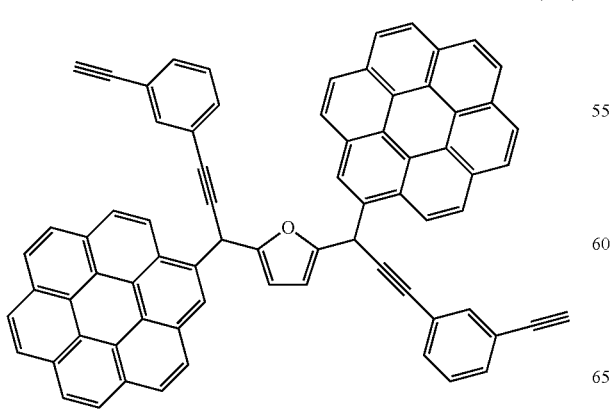
(A-6)
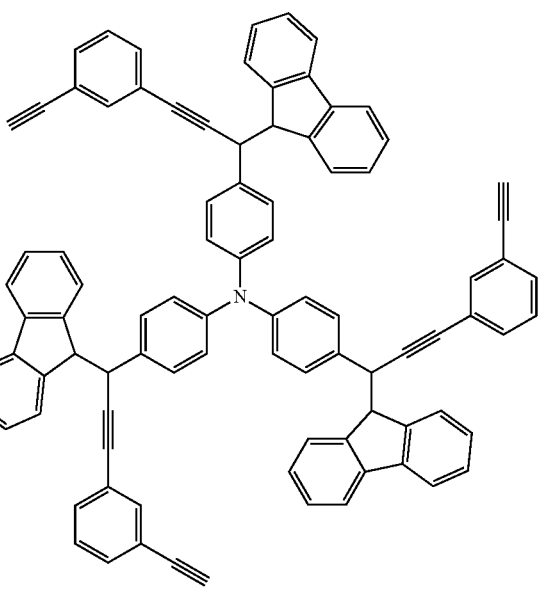

(A-7)

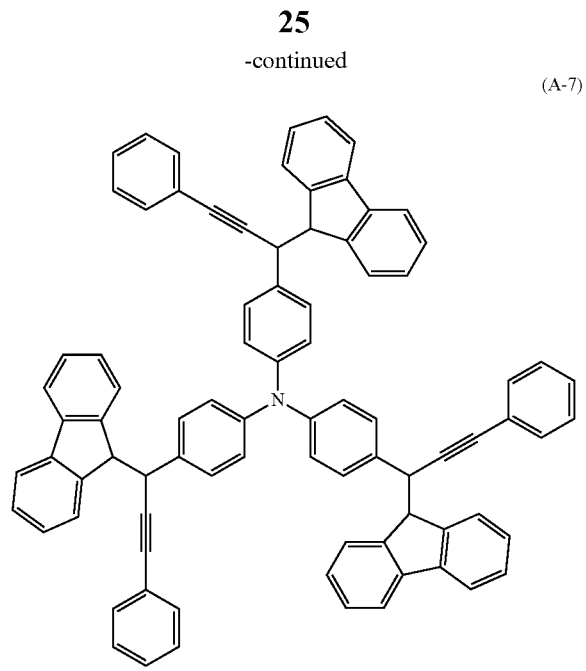

(a-3)

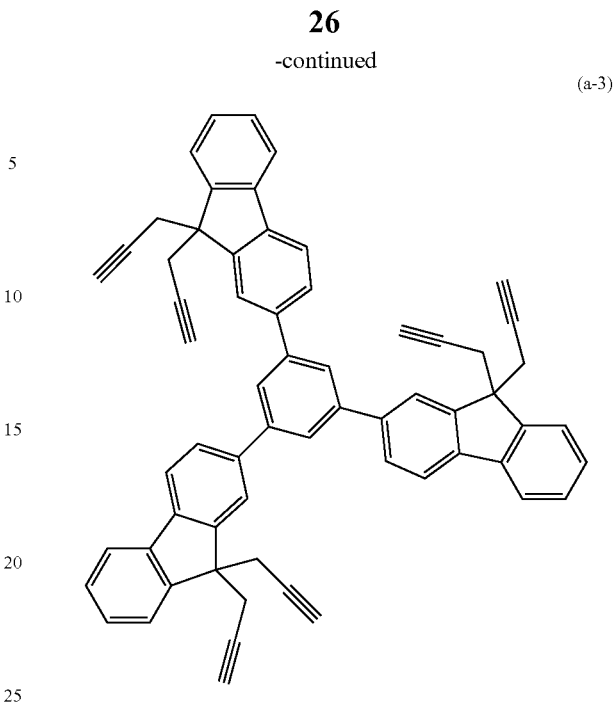

(a-1)

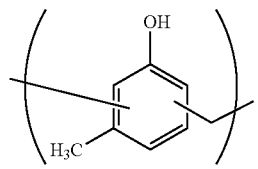

(a-2)

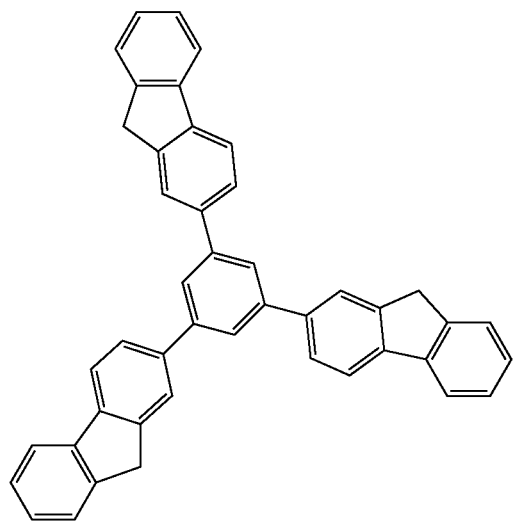

Synthesis Example 1: Synthesis of Compound (A-1)

Into a reaction vessel were charged 3.3 g of m-diethynylbenzene and 20 g of tetrahydrofuran (hereinafter, may be also referred to as "THF") in a nitrogen atmosphere, and then 12 ml of a 2.0 M ethyl magnesium chloride/THF solution was added at −30° C. A reaction was permitted at −30° C. for 1 hour, and then 5.0 g of 1-formylpyrene was added thereto and a reaction was permitted at −30° C. for 1 hour, followed by heating to room temperature and permitting a reaction for 1 hour. The reaction was terminated with a 1 N hydrochloric acid solution, an organic layer was washed with water, and then reprecipitation was permitted with hexane to give an intermediate being in a form of an alcohol. Into a reaction vessel, 0.8 g of triphenylamine, 3.5 g of the intermediate, 0.1 g of pyridinium p-toluenesulfone, and 13 g of THF were charged in a nitrogen atmosphere, and a reaction was permitted at 80° C. for 3 hrs. Reprecipitation was permitted with methanol to give the compound (A-1) (molecular weight: 1,261).

Synthesis Example 2: Synthesis of Compound (A-2)

Into a reaction vessel were charged 3.9 g of 1,3,5-triethynylbenzene and 20 g of THF in a nitrogen atmosphere, and then 12 ml of a 2.0 M ethyl magnesium chloride/THF solution was added at −30° C. A reaction was permitted at −30° C. for 1 hour, and then 5.0 g of 1-formylpyrene was added thereto and a reaction was permitted at −30° C. for 1 hour, followed by heating to room temperature and permitting a reaction for 1 hour. The reaction was terminated with a 1 N hydrochloric acid solution, an organic layer was washed with water, and then reprecipitation was permitted with hexane to give an intermediate being in a form of an alcohol. Into a reaction vessel, 0.8 g of 2,6-dihydroxynaphthalene, 3.8 g of the intermediate, 0.2 g of pyridinium p-toluenesulfone, and 14 g of THF were charged in a nitrogen atmosphere, and a reaction was permitted at 80° C. for 3 hrs. Reprecipitation was permitted with methanol to give the compound (A-2) (molecular weight: 885).

Synthesis Example 3: Synthesis of Compound (A-3)

Into a reaction vessel were charged 2.7 g of m-diethynylbenzene and 20 g of THF in a nitrogen atmosphere, and then 8.4 ml of a 2.0 M ethyl magnesium chloride/THF solution was added at −30° C. A reaction was permitted at −30° C. for 1 hour, and then 5.0 g of 1-corenene carbaldehyde was added thereto and a reaction was permitted at −30° C. for 1 hour, followed by heating to room temperature and permitting a reaction for 1 hour. The reaction was terminated with a 1 N hydrochloric acid solution, an organic layer was washed with water, and then reprecipitation was permitted with hexane to give an intermediate being in a form of an alcohol. Into a reaction vessel, 0.3 g of furan, 4.0 g of the intermediate, 0.2 g of pyridinium p-toluenesulfone, and 13 g of THF were charged in a nitrogen atmosphere, and a reaction was permitted at 80° C. for 3 hrs. Reprecipitation was permitted with methanol to give the compound (A-3) (molecular weight: 941).

Synthesis Example 4: Synthesis of Compound (A-4)

Into a reaction vessel were charged 3.7 g of m-diethynylbenzene and 20 g of THF in a nitrogen atmosphere, and then 14 ml of a 2.0 M ethyl magnesium chloride/THF solution was added at −30° C. A reaction was permitted at −30° C. for 1 hour, and then 5.0 g of p-trimethylsilylethynylbenzaldehyde was added thereto and a reaction was permitted at −30° C. for 1 hour, followed by heating to room temperature and permitting a reaction for 1 hour. THF was removed in vacuo, followed by charging 15 ml of methanol and 3 g of sodium hydroxide and permitting a reaction at room temperature for 1 hour. The reaction solution was neutralized with a 1 N hydrochloric acid solution, an organic layer was washed with water, and then reprecipitation was permitted with hexane to give an intermediate being in a form of an alcohol. Into a reaction vessel, 0.4 g of pyrrole, 3.1 g of the intermediate, 0.2 g of pyridinium p-toluenesulfone, and 10 g of THF were charged in a nitrogen atmosphere, and a reaction was permitted at 80° C. for 3 hrs. Reprecipitation was permitted with methanol to give the compound (A-4) (molecular weight: 544).

Synthesis Example 5: Synthesis of Compound (A-5)

Into a reaction vessel were charged 4.1 g of 9-ethynylphenanthrene and 23 g of THF in a nitrogen atmosphere, and then 9.2 ml of a 2.0 M ethyl magnesium chloride/THF solution was added at −30° C. A reaction was permitted at −30° C. for 1 hour, and then 5.0 g of 3,5-bis(trimethylsilylethynyl)benzaldehyde was added thereto and a reaction was permitted at −30° C. for 1 hour, followed by heating to room temperature and permitting a reaction for 1 hour. THF was removed in vacuo, followed by charging 15 ml of methanol and 3 g of sodium hydroxide and permitting a reaction at room temperature for 1 hour. The reaction solution was neutralized with a 1 N hydrochloric acid solution, an organic layer was washed with water, and then reprecipitation was permitted with hexane to give an intermediate being in a form of an alcohol. Into a reaction vessel, 0.8 g of 9,9-bis(4-hydroxyphenyl)fluorene, 1.6 g of the intermediate, 0.1 g of pyridinium p-toluenesulfone, and 10 g of THF were charged in a nitrogen atmosphere, and a reaction was permitted at 80° C. for 3 hrs. Reprecipitation was permitted with methanol to give the compound (A-5) (molecular weight: 1,027).

Synthesis Example 6: Synthesis of Compound (A-6)

The compound (A-6) (molecular weight: 1,152) was obtained by a similar operation to that of Synthesis Example 1, except that fluorene-9-carbaldehyde was used in place of 1-formylpyrene.

Synthesis Example 7: Synthesis of Compound (A-7)

The compound (A-7) (molecular weight: 1,080) was obtained by a similar operation to that of Synthesis Example 1, except that fluorene-9-carbaldehyde was used in place of 1-formylpyrene, and phenylacetylene was used in place of m-diethynylbenzene.

Synthesis Example 8: Synthesis of Polymer (a-1)

Into a reaction vessel were charged 250.0 g of m-cresol, 125.0 g of 37% by mass formalin, and 2 g of anhydrous oxalic acid in a nitrogen atmosphere, and a reaction was allowed at 100° C. for 3 hrs and at 180° C. for 1 hour. Thereafter, the unreacted monomer was removed under reduced pressure to give the polymer (a-1). The Mw of the polymer (a-1) thus obtained was 11,000.

Synthesis Example 9: Synthesis of Compound (a-2)

Into a reaction vessel were charged 20.0 g of 2-acetylfluorene and 20.0 g of m-xylene in a nitrogen atmosphere, and dissolution was permitted at 110° C. Next, 3.14 g of dodecylbenzenesulfonic acid was added, a resulting solution was heated to 140° C., and a reaction was permitted for 16 hrs. After completion of the reaction, the reaction liquid was diluted by adding 80 g of xylene, followed by cooling to 50° C. and charging into 500 g of methanol to permit reprecipitation. A thus obtained precipitate was washed with toluene and a solid was collected on a filter paper and dried to give the compound (a-2).

Synthesis Example 10: Synthesis of Compound (a-3)

Into a reaction vessel were charged 10.0 g of the compound (a-2), 18.8 g of propargyl bromide, and 50 g of toluene in a nitrogen atmosphere, followed by stirring. To a thus resulting solution were added 25.2 g of a 50% by mass aqueous sodium hydroxide solution and 1.7 g of tetrabutylammonium bromide, and a reaction was permitted at 92° C. for 12 hrs. The reaction liquid was cooled to 50° C., and then 25 g of THF was added thereto. An aqueous layer was removed, followed by charging 50 g of a 1% by mass aqueous oxalic acid solution and conducting extraction by liquid separation, and then charging into hexane to permit reprecipitation. The precipitate was collected on a filter and then dried to give the compound (a-3) (molecular weight: 798).

Preparation of Composition for Forming Resist Underlayer Film

The compound (A), the solvent (B), the acid generating agent (C), and the crosslinking agent (D) used in preparing the composition are shown below.

(A) Composition
  Examples: Above-Synthesized Compounds (A-1) to (A-5)
  Comparative Examples: Above-Synthesized Polymer (a-1) and Above-Synthesized Compound (a-3)

(B) Solvent
  B-1: propylene glycol monomethyl ether acetate
  B-2: cyclohexanone (C) Acid Generating Agent
  C-1: bis(4-t-butylphenyl)iodonium nonafluoro-n-butane-sulfonate (a compound represented by the following formula (C-1))

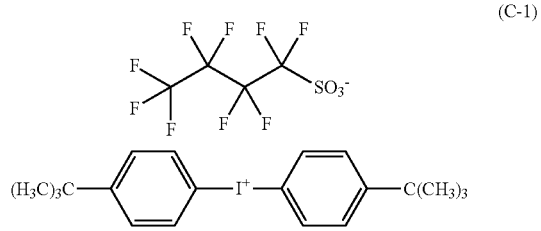

(D) Crosslinking Agent
  D-1: 1,3,4,6-tetrakis(methoxymethyl)glycoluril (a compound represented by the following formula (D-1))

(D-1)

Example 1

10 parts by mass of (A-1) as the compound (A) were dissolved in 90 parts by mass of (B-1) as the solvent (B). A resulting solution was filtered through a polytetrafluoroethylene (PTFE) membrane filter having a pore size of 0.45 m to prepare a composition for forming a resist underlayer film (J-1).

Examples 2 to 8 and Comparative Examples 1 to 2

Compositions for forming resist underlayer films (J-2) to (J-8) and (CJ-1) to (CJ-2) were prepared in a similar manner to Example 1, except that for each component, the type and content shown in Table 1 below, was used. "–" in the "(C) Acid generating agent" and "(D) Crosslinking agent" columns in Table 1 indicates that the corresponding component was not used. "Proportion of hydrogen atoms" in Table 1 indicates a proportion of hydrogen atoms with respect to total atoms constituting the compound (A), and is a value calculated from the molecular formula of the compound (A). "–" in the "proportion of hydrogen atoms" column in Table 1 indicates that the proportion of hydrogen atoms was not calculated.

TABLE 1

| | Composition for forming resist underlayer film | (A) Compound | | | (B) Solvent | | (C) Acid generating agent | | (D) Crosslinking agent | |
|---|---|---|---|---|---|---|---|---|---|---|
| | | type | proportion of hydrogen atoms (% by mass) | content (parts by mass) | type | content (parts by mass) | type | content (parts by mass) | type | content (parts by mass) |
| Example 1 | J-1 | A-1 | 4.6 | 10 | B-1 | 90 | — | — | — | — |
| Example 2 | J-2 | A-2 | 4.1 | 10 | B-1 | 90 | — | — | — | — |
| Example 3 | J-3 | A-3 | 3.9 | 10 | B-1 | 90 | — | — | — | — |
| Example 4 | J-4 | A-4 | 4.6 | 10 | B-1 | 90 | — | — | — | — |
| Example 5 | J-5 | A-5 | 4.5 | 10 | B-1 | 90 | — | — | — | — |
| Example 6 | J-6 | A-1 | 4.6 | 10 | B-1/B-2 | 50/40 | — | — | — | — |
| Example 7 | J-7 | A-1 | 4.6 | 10 | B-1 | 90 | C-1 | 0.5 | — | — |
| Example 8 | J-8 | A-1 | 4.6 | 10 | B-1 | 90 | C-1 | 0.5 | D-1 | 3 |
| Comparative Example 1 | CJ-1 | a-1 | — | 10 | B-1 | 90 | C-1 | 0.5 | D-1 | 3 |
| Comparative Example 2 | CJ-2 | a-3 | 5.3 | 10 | B-1 | 90 | — | — | — | — |

Formation of Resist Underlayer Film

Each composition for forming a resist underlayer film prepared as described above was applied on a silicon wafer (substrate) with a spin coater ("CLEAN TRACK ACT 12," available from Tokyo Electron Limited) by way of a spin-coating procedure. Next, heating in an ambient air atmosphere at the heating temperature (° C.) for the heating time period (sec) shown in Table 2 below was followed by cooling at 23° C. for 60 sec to form a resist underlayer film having an average thickness of 200 nm. Accordingly, a resist underlayer film-attached substrate, in which the resist underlayer film was formed on the substrate, was obtained.

Evaluations

By using the compositions for forming resist underlayer films and the resist underlayer film-attached substrates, each obtained as described above, etching resistance, heat resistance, flatness, and flexural resistance were evaluated according to the following procedures. The results of the evaluations are shown together in Table 2 below.

Etching Resistance

The resist underlayer film of the resist underlayer film-attached substrate obtained as described above was treated in an etching apparatus ("TACTRAS," available from Tokyo Electron Limited) under conditions involving: $CF_4/Ar=110/440$ sccm, PRESS.=30 MT, HF RF (radiofrequency power for plasma production)=500 W, LF RF (radiofrequency power for bias)=3,000 W, DCS=−150 V, RDC (flow rate percentage at gas center)=50%, and 30 sec. An etching rate (nm/min) was calculated based on the average thickness of the resist underlayer film before the treatment and the average thickness of the resist underlayer film after the treatment. Next, with the etching rate of Comparative Example 2 being the standard, a ratio with respect to Comparative Example 2 was determined as a marker for etching resistance evaluation. The etching resistance was evaluated to be: "A" (extremely favorable) in a case in which the ratio was less than 0.95; "B" (favorable) in a case in which the ratio was no less than 0.95 and less than 1.00; and "C" (unfavorable) in a case in which the ratio was no less than 1.00. It is to be noted that in Table 2, "-" indicates being a standard for the etching resistance.

Heat Resistance

The resist underlayer film of the thus obtained resist underlayer film-attached substrate was scraped to collect a powder, the powder of the resist underlayer film was placed into a container used for measurement by a TG-DTA apparatus ("TG-DTA 2000SR," available from NETZSCH), and a mass of the powder prior to heating was measured. The powder was then heated to 400° C. in the TG-DTA apparatus in a nitrogen atmosphere with a rate of temperature rise of 10° C./min, and the mass of the powder was measured upon reaching 400° C. The mass loss rate (%) was obtained by the following equation and defined as a marker of heat resistance.

$$M_L=\{(m1-m2)/m1\} \times 100$$

In the above equation, $M_L$ represents the mass loss rate (%); m1 represents the mass prior to heating (mg); and m2 represents the mass at 400° C. (mg).

A lower mass loss rate of the powder used as the sample indicates that the heat resistance is more favorable, due to less generation of sublimated matter and resist underlayer film degradation products during the heating of the resist underlayer film. In other words, the lower mass loss rate indicates higher heat resistance. The heat resistance was evaluated to be: "A" (extremely favorable) in a case in which the mass loss rate was less than 5%; "B" (favorable) in a case in which the mass loss rate was no less than 5% and less than 10%; and "C" (unfavorable) in a case in which the mass loss rate was no less than 10%.

Flatness

Each of the compositions for forming resist underlayer films prepared as described above was applied by a spin-coating procedure using the spin coater, on a silicon substrate 1 provided with a trench pattern having a depth of 100 nm and a groove width of 10 μm formed thereon, as shown in FIG. 1. A rotational speed for the spin coating was the same as that in the case of forming the resist underlayer film having the average thickness of 200 nm in "Formation of Resist Underlayer Film" described above. Subsequently, by heating (baking) in an ambient air atmosphere at a heating temperature (° C.) for a heating time period (sec) shown in Table 2 below, a resist underlayer film 2 was formed having an average thickness of 200 nm at parts having no trench provided. Accordingly, a film-attached silicon substrate, the silicon substrate 1 being covered by the resist underlayer film 2, was obtained.

A cross-sectional shape of the film-attached silicon substrate was observed by using a scanning electron microscope ("S-4800," available from Hitachi High-Technologies Corporation), and the difference (AFT) between a height at a center portion "b" of the trench pattern of the resist underlayer film 2 and a height at a position "a" 5 m away from the edge of the trench pattern, at which no trench pattern was provided, was defined as a marker of the flatness. The flatness was evaluated to be: "A" (favorable) in a case of AFT being less than nm; "B" (somewhat favorable) in a case of AFT being no less than 35 nm and less than 60 nm; and "C" (unfavorable) in a case of AFT being no less than 60 nm. It is to be noted that the difference in heights shown in FIG. 1 is exaggerated.

Flexural Resistance

Film-attached substrates with each of the resist underlayer films formed thereon, the resist underlayer films each having an average thickness of 200 nm, were obtained by: applying, using the spin coater, on silicon substrates each having a silicon dioxide film with an average thickness of 500 nm being formed thereon, each of the compositions for forming resist underlayer films prepared as described above; and then baking in an ambient atmosphere at 350° C. for 60 sec. On the film-attached substrates obtained as described above, a composition for silicon-containing film formation ("NFC SOG080" available from JSR Corporation) was applied by a spin-coating procedure and then heated (baked) at 200° C. for 60 sec in an ambient air atmosphere, followed by additional heating at 300° C. for 60 sec to form a silicon-containing film having an average thickness of 50 nm. On the silicon-containing film, a resist composition for ArF ("AR1682J," available from JSR Corporation) was applied by a spin-coating procedure and then heated at 130° C. for 60 sec in an ambient air atmosphere to form a resist film having an average thickness of 200 nm. The resist film was subjected to an exposure with an exposure dose altered through a 1:1 line-and-space mask pattern with a target size of 100 nm by using an ArF excimer laser lithography device (lens numerical aperture: 0.78; exposure wavelength: 193 nm), and then heated (baked) at 130° C. for 60 sec in an ambient air atmosphere. A development was carried out with a 2.38% by mass aqueous tetramethylammonium hydroxide (TMAH) solution at 25° C. for 1 min, followed by washing with water and drying. Accordingly, a line-and-space resist-patterned substrate with a pitch of 200 nm was obtained having a line width of the line pattern being from 30 nm to 100 nm.

Using the resist pattern as a mask, the silicon-containing film was etched with the etching apparatus under a condition of $CF_4$=200 sccm, PRESS.=85 mT, HF RF (high-frequency power for plasma production)=500 W, LF RF (high-frequency power for bias)=0 W, DCS=−150 V, and RDC (proportion of gas center flow rate)=50% to give a substrate patterned on the silicon-containing film. Next, using the silicon-containing film pattern as a mask, the resist underlayer film was etched with the etching apparatus under a condition of $O_2$=400 sccm, PRESS.=25 mT, HF RF (high-frequency power for plasma production)=400 W, LF RF (high-frequency power for bias)=0 W, DCS=0 V, and RDC (proportion of gas center flow rate)=50% to give the substrate patterned on the resist underlayer film. Using the resist underlayer film pattern as a mask, the silicon dioxide film was etched with the etching apparatus under a condition of CF$_4$=180 sccm, Ar=360 sccm, PRESS.=150 mT, HF RF (high-frequency power for plasma production)=1,000 W, LF RF (high-frequency power for bias)=1,000 W, DCS=−150 V, and RDC (proportion of gas center flow rate)=50%, for 60 sec to give the substrate patterned on the silicon dioxide film.

Figure 2:
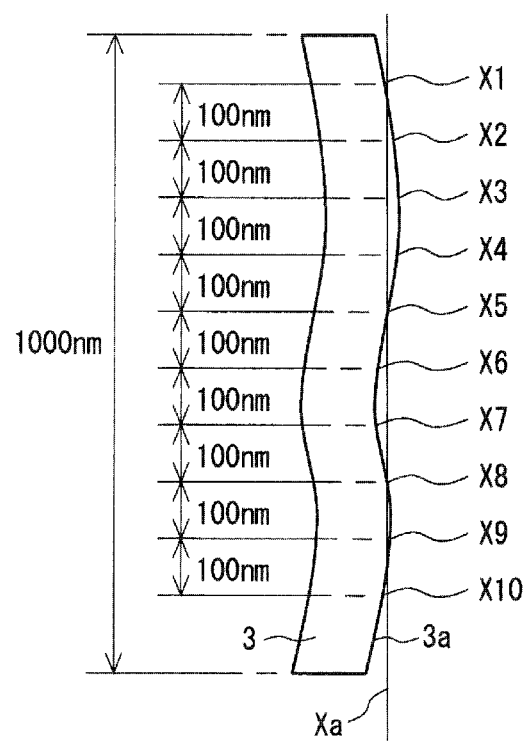
FIG. 2 is a schematic plan view for illustrating a flexural resistance evaluation method.

Thereafter, with regard to the substrate patterned on the silicon dioxide film, a 250,000 times enlarged image of the configuration of the resist underlayer film pattern with each line width was obtained by a scanning electron microscope ("CG-4000," available from Hitachi High-Technologies Corporation), and image processing thereof was executed. Accordingly, as shown in FIG. 2, LER (line-edge roughness) was determined on a side lateral face 3a of a resist underlayer film pattern 3 (line pattern) with a length of 1,000 nm in the configuration thus observed, in terms of a 3 Sigma value derived by triplicating a standard deviation calculated from: positions Xn (n=1 to 10) in a line width direction measured at ten points with intervals of 100 nm; and a position Xa corresponding to an average of these positions in the line width direction. LER, indicating a degree of bending of the resist underlayer film pattern, increases as the line width of the resist underlayer film pattern decreases. On the basis of the line width of the resist underlayer film pattern that results in LER of 5.5 nm, the flexural resistance was evaluated to be: "A" (favorable) in a case in which this line width was less than 40.0 nm; and "B" (unfavorable) in a case in which this line width was no less than 40.0 nm. It is to be noted that the bending feature of the resist underlayer film pattern shown in FIG. 2 is exaggeratedly illustrated.

TABLE 2

| | Composition for forming resist underlayer film | Temperature/time period when forming resist underlayer film (° C./sec) | Etching resistance | Heat resistance | Flatness | Flexural resistance |
|---|---|---|---|---|---|---|
| Example 1 | J-1 | 250/60 | A | A | A | A |
| Example 2 | J-2 | 250/60 | A | A | A | A |
| Example 3 | J-3 | 250/60 | A | A | A | A |
| Example 4 | J-4 | 250/60 | A | A | A | A |
| Example 5 | J-5 | 250/60 | A | A | A | A |
| Example 6 | J-6 | 250/60 | A | A | A | A |
| Example 7 | J-7 | 250/60 | A | A | A | A |
| Example 8 | J-8 | 250/60 | B | B | B | A |
| Comparative Example 1 | CJ-1 | 250/60 | C | C | C | B |
| Comparative Example 2 | CJ-2 | 250/60 | — | B | B | B |

As is seen from the results shown in Table 2, the resist underlayer films formed from the compositions for forming resist underlayer films of the Examples were superior to the resist underlayer films formed from the compositions for forming resist underlayer films of the Comparative Examples in the etching resistance, the heat resistance, the flatness, and the flexural resistance.

The composition for forming a resist underlayer film of the embodiment of the present invention enables forming a resist underlayer film being superior in etching resistance, heat resistance, flatness, and flexural resistance. The resist underlayer film of the embodiment of the present invention is superior in etching resistance, heat resistance, flatness, and flexural resistance. The method of forming a resist underlayer film of the embodiment of the invention enables forming a resist underlayer film being superior in etching resistance, heat resistance, flatness, and flexural resistance.

The method of forming a patterned substrate of the embodiment of the present invention enables obtaining a favorable patterned substrate. The compound of the embodiment of the present invention can be favorably used as a component of the composition of the embodiment of the present invention. Therefore, these can be suitably used in the manufacture of semiconductor devices and the like, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:
1. A composition comprising:
a compound represented by formula (2); and
a solvent,

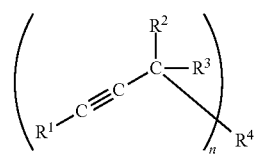

(2)

wherein, in the formula (1), R$^1$ and R$^2$ each independently represent a substituted or unsubstituted aryl group having 6 to 30 ring atoms or a substituted or unsubstituted heteroaryl group having 5 to 30 ring atoms; at least one of R$^1$ and R$^2$ represents a substituted or unsubstituted naphthyl group, a substituted or unsubstituted anthryl group, a substituted or unsubstituted fluorenyl group, a substituted or unsubstituted phenanthryl group, a substituted or unsubstituted phenalenyl group, a substituted or unsubstituted pyrenyl group, a substituted or unsubstituted chrysenyl group, a substituted or unsubstituted triphenylenyl group, a substituted or unsubstituted tetracenyl group, a substituted or unsubstituted perylenyl group, a substituted or unsubstituted picenyl group, a substituted or unsubstituted pentacenyl group, a substituted or unsubstituted hexacenyl group, a substituted or unsubstituted coronenyl group, a substituted or unsubstituted trinaphthylenyl group, a substituted or unsubstituted heptacenyl group, or a substituted or unsubstituted heteroaryl group having 5 to 30 ring atoms; R$^3$ represents a hydrogen atom or a substituted or unsubstituted monovalent aliphatic hydrocarbon group having 1 to 10 carbon atoms; n is an integer of 2 to 10, wherein a plurality of $R^1$s are identical or different from each other, a plurality of $R^2$s are identical or different from each other, and a plurality of $R^3$s are identical or different from each other; and $R^4$ represents an organic group having a valency of n and having an aromatic ring which has 5 to 40 ring atoms.

2. The composition according to claim 1, wherein the substituted or unsubstituted monovalent aliphatic hydrocarbon group which is represented by $R^3$ is a substituted or unsubstituted monovalent chain hydrocarbon group.

3. The composition according to claim 1, wherein $R^3$ represents a hydrogen atom.

4. The composition according to claim 1, wherein at least one of $R^1$ and $R^2$ represents a group represented by formula (3):

(3)

wherein, in the formula (3), $R^5$ represents a hydrogen atom or a monovalent aliphatic hydrocarbon group having 1 to 10 carbon atoms; Ar represents a group obtained by removing (m+1) hydrogen atoms from an aromatic ring having 6 to 30 ring atoms; m is an integer of 1 to 3; ** denotes a binding site to a carbon atom to which $R^1$ or $R^2$ bonds in the formula (1);

and in a case in which m is no less than 2, a plurality of $R^5$s are identical or different from each other.

5. The composition according to claim 1, wherein a proportion of hydrogen atoms with respect to all atoms constituting the compound is no greater than 7% by mass.

6. The composition according to claim 1, wherein a molecular weight of the compound is no less than 300 and no greater than 3,000.

7. A method of forming a resist underlayer film, the method comprising:
applying the composition according to claim 1 directly or indirectly on a substrate.

8. A method of producing a patterned substrate, the method comprising:
forming a resist underlayer film directly or indirectly on a substrate by applying the composition according to claim 1;
forming a resist pattern directly or indirectly on the resist underlayer film; and
carrying out etching using the resist pattern as a mask.

9. The method according to claim 8, further comprising, before forming the resist pattern, forming a silicon-containing film directly or indirectly on the resist underlayer film formed.

10. A compound represented by formula (2):

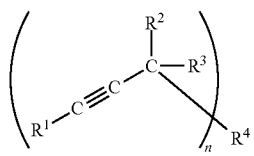

(2)

wherein, in the formula (2), $R^1$ and $R^2$ each independently represent a substituted or unsubstituted aryl group having 6 to 30 ring atoms or a substituted or unsubstituted heteroaryl group having 5 to 30 ring atoms; at least one of $R^1$ and $R^2$ represents a substituted or unsubstituted naphthyl group, a substituted or unsubstituted anthryl group, a substituted or unsubstituted fluorenyl group, a substituted or unsubstituted phenanthryl group, a substituted or unsubstituted phenalenyl group, a substituted or unsubstituted pyrenyl group, a substituted or unsubstituted chrysenyl group, a substituted or unsubstituted triphenylenyl group, a substituted or unsubstituted tetracenyl group, a substituted or unsubstituted perylenyl group, a substituted or unsubstituted picenyl group, a substituted or unsubstituted pentacenyl group, a substituted or unsubstituted hexacenyl group, a substituted or unsubstituted coronenyl group, a substituted or unsubstituted trinaphthylenyl group, a substituted or unsubstituted heptacenyl group, or a substituted or unsubstituted heteroaryl group having 5 to 30 ring atoms; $R^3$ represents a hydrogen atom or a substituted or unsubstituted monovalent aliphatic hydrocarbon group having 1 to 10 carbon atoms; n is an integer of 2 to 10, wherein a plurality of $R^1$s are identical or different from each other, a plurality of $R^2$s are identical or different from each other, and a plurality of $R^3$s are identical or different from each other; and $R^4$ represents an organic group having a valency of n and having an aromatic ring which has 5 to 40 ring atoms.

11. The composition according to claim 1, wherein at least one of $R^1$ and $R^2$ represents a substituted or unsubstituted fluorenyl group or a substituted or unsubstituted pyrenyl group.

12. The compound according to claim 10, wherein at least one of $R^1$ and $R^2$ represents a substituted or unsubstituted fluorenyl group or a substituted or unsubstituted pyrenyl group.

13. The compound according to claim 10, wherein the substituted or unsubstituted monovalent aliphatic hydrocarbon group which is represented by $R^3$ is a substituted or unsubstituted monovalent chain hydrocarbon group.

14. The compound according to claim 10, wherein $R^3$ represents a hydrogen atom.

15. The composition according to claim 1, wherein $R^4$ represents a group represented by formula (II-1), formula (II-2), formula (II-3), formula (II-4), or formula (II-5):

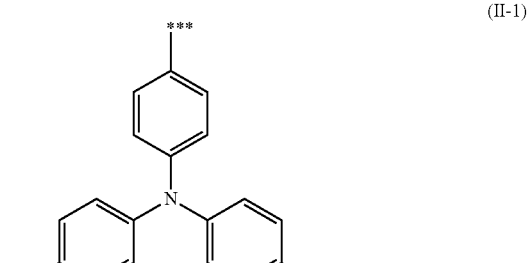

(II-1)

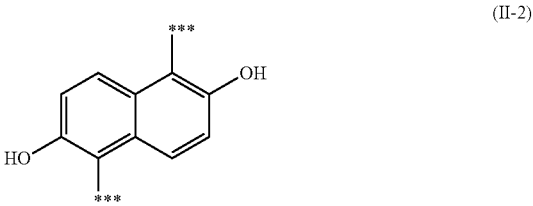

(II-2)

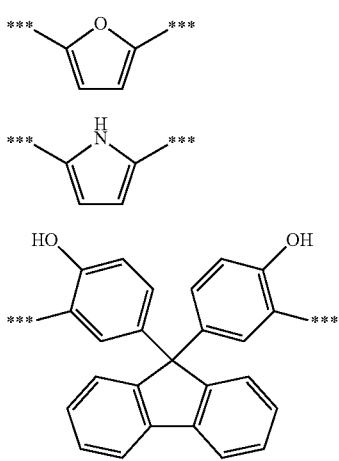
(II-3)
(II-4)
(II-5)
wherein ** denotes a binding site to a carbon atom to which $R^4$ in the formula (2) bonds.
16. The compound according to claim 10, wherein $R^4$ represents a group represented by formula (II-1), formula (II-2), formula (II-3), formula (II-4), or formula (II-5):
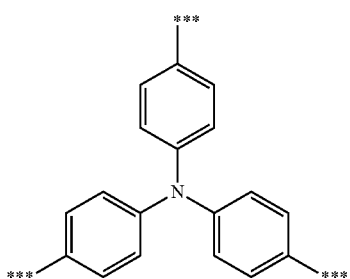
(II-1)
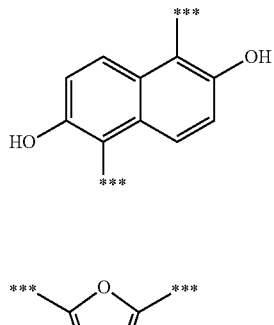
(II-2)
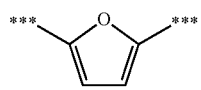
(II-3)
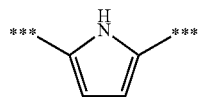
(II-4)
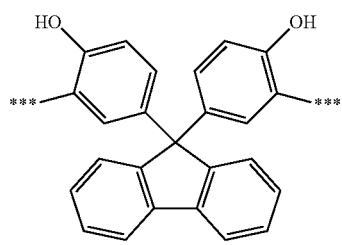
(II-5)
wherein *** denotes a binding site to a carbon atom to which $R^4$ in the formula (2) bonds.
* * * * *